United States Patent [19]

Kray et al.

[11] 4,307,024

[45] Dec. 22, 1981

[54] 1,1,1-TRIARYL-2,2,2-TRIFLUOROETHANES AND PROCESS FOR THEIR SYNTHESIS

[76] Inventors: Robert A. Frosch, Administrator of the National Aeronautics and Space Administration, with respect to an invention of William D. Kray, Burnt Hills, N.Y.; Robert W. Rosser, San Jose, Calif.

[21] Appl. No.: 891,872

[22] Filed: Mar. 30, 1978

[51] Int. Cl.$^3$ ..................... C07C 17/00; C07C 17/24; C07C 17/26; C07C 19/08
[52] U.S. Cl. .................................. 260/389; 260/386; 570/123; 570/129; 528/402
[58] Field of Search ............... 260/389, 386; 1/668 R; 570/123, 129

[56] References Cited

PUBLICATIONS

Hey et al., Chemical Abstracts, vol. 54, Cols. 8710 to 8714 (1960).
Steadman, Chemical Abstracts, vol. 79, Item 104937h (1973).
Kray et al., J. Organic Chemistry, vol. 42, No. 7, pp. 1186 to 1189 (1977).

*Primary Examiner*—Floyd D. Higel
*Attorney, Agent, or Firm*—Darrell G. Brekke; John R. Manning

[57] ABSTRACT

New 1,1,1-triaryl-2,2,2-trifluoroethanes in which the aryl radicals carry one or more substitutents have been prepared by condensation of trifluoroacetophenones with substituted phenyl compounds in the presence of catalytic quantities of trifluoromethylsulfonic acid. The reaction can be carried out under reflux in toluene or, for strikingly better results in certain cases, reactants are simply stirred at room temperature for about 24 to 48 hours.

6 Claims, No Drawings

1,1,1-TRIARYL-2,2,2-TRIFLUOROETHANES AND PROCESS FOR THEIR SYNTHESIS

ORIGIN

The invention described herein was made in the performance of work under a NASA contract and is subject to the provisions of Section 305 of the National Aeronautics and Space Act of 1958, Public Law 85-568 (72 Stat. 435; 42 U.S.C. 2457).

THE PRIOR ART

While the literature is replete with examples of multifunctional triarylmethanes and carbinols, no triaryltrifluoroethanes have yet been described.

Some of the compounds of the art, triarylcarbinols, have been prepared by a reaction involving a diarylketone, a halogenated aromatic compound, an alkali metal and hot benzene (Coffee, U.S. Pat. No. 1,873,290). Shen et al., on the other hand, teach the formation of multifunctional triaryldifluoroethanes by the action of difluorocarbene on a suitable carbanion in a basic medium, followed by protonation (U.S. Pat. No. 3,221,007).

As to ethanes, multisubstituted triaryl-α,α,α-trichloroethanes have been mentioned [D. A. Hey and J. Peters, J. Chem. Soc., 79 (1960)], but the method used to prepare them does not lend itself to large scale production, nor is it directly applicable to the synthesis of the desired trifluoro analogs.

Finally, such compounds as 1,1,1-tris-(4-aminophenyl) methane [S. Patai and S. Doyagi, J. Chem. Soc., 3058 (1958)] have been prepared from a ketone or an aldehyde by hydroxyalkylation. The process, in which the ketone or aldehyde is first protonated with an acid catalyst to act as an electrophile for aromatic substitution, often proceeds without control until high polymers, such as phenol-formaldehyde resins, are formed [Cram et al., "Organic Chemistry," 385–387 (1959)]. Also, as shown by Lodolini et al., some aminotriphenylmethanes can be prepared in good yields from aromatic aldehydes using organic sulfonic acids such as methylsulfonic acid, as catalyst (U.S. Pat. No. 3,739,000).

SUMMARY OF THE INVENTION

It has now been discovered that new multifunctional triaryl-2,2,2-trifluoroethanes can be prepared in good yield and purity from trifluoroacetophenones by condensation with substituted aryl compounds in the presence of catalytic quantities of trifluoromethylsulfonic acid. The reaction may be carried out under reflux conditions in an organic liquid such as toluene or, preferably in certain cases, the reaction mixture is simply agitated at ambient temperature for a period of about 24 to 48 hours. The compounds that can be thus obtained have the formula

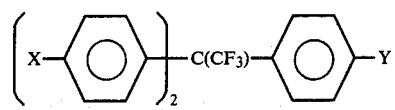

in which X and Y can be either hydrogen or halogen atoms, or various radicals such as methoxy, phenoxy, lower alkyl groups containing up to about 5 carbon atoms, halogenated alkyl groups such as trifluoromethyl, amino, carboxy, nitrile, formyl, acetamido, and other groups of that general type.

DETAILED DESCRIPTION OF THE INVENTION

The new multifunctional triaryl-2,2,2-trifluoroethanes of this invention were prepared by an hydroxyalkylation condensation reaction in which a trifluoroacetophenone combines with aryl compounds in the presence of catalytic quantities of trifluoromethylsulfonic acid (TFMS). The reaction may be carried out in a liquid such as toluene at reflux temperature. It has been found, however, that significantly greater yields of high purity products can be obtained with simple agitation of the reactants at ambient temperature for a period of time sufficient for the species involved. It has also been discovered further that certain reactions will proceed at ambient temperature that are not favored at all under toluene reflux conditions.

In any event, the formation of the compounds of this invention is believed to proceed according to a mechanism which involves the agency of strongly electrophilic carbonium ions. The overall reaction can be illustrated as follows, with toluene being employed as the aryl compound which combines with trifluoroacetophenone:

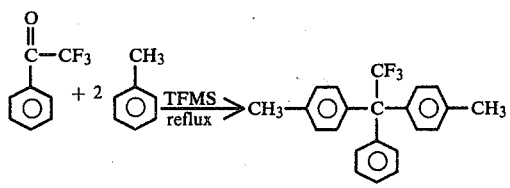

When the above described reaction is carried out with agitation at ambient temperatures, the yield of pure tritolylethane increase surprisingly from about 43% to 93%, based on the acetophenone.

When certain aryl compounds such as anisole, benzene, bromobenzene and ethylbenzene, are substituted for toluene under conditions similar to those described in the equation shown above, only complex, generally tarry mixtures are obtained.

When, on the other hand, the reaction is allowed to proceed at ambient temperature with agitation for a period that may vary from about 24 hours to about 48 hours depending on the particular reactants employed, useful products can be obtained in good to excellent yields. Interestingly, the attempted use of a variety of nonvolatile acids such as sulfuric, phosphoric and polyphosphoric acids has failed to yield any significant quantity of recoverable triaryltrifluoroethane. Attempts to obtain a triarylfluoroalkane from 4-methylheptabutyrophenone were also unsuccessful, yielding the ditolyl heptafluoropropylcarbinol that could be expected from the relevant prior art.

As shown by several of the embodiments that shall be described hereinafter, various functional groups of the new triarylfluoroethanes disclosed can be converted by conventional means to other functional groups, thus creating new compounds which in some cases could be obtained directly from the condensation reaction of an acetophenone with appropriate aryl compounds and which, in other cases could not be so obtained due to the chemical properties of the particular aryl compounds involved.

The invention will now be illustrated in operational detail by means of the following examples which describe, inter alia, preferred embodiments of the processes and products involved. Unless otherwise noted, all quantities and percentages given are on a weight basis. Melting points have been determined with a Mel-Temp apparatus and are uncorrected. IR and NMR spectra were taken on a Perkin Elmer-180 and a Varian HA-100, respectively. Mass spectra were obtained on a Bell & Howell-21-491 at 70 eV.

EXAMPLE 1

1-Phenyl-1,1-bis-(p-tolyl)-2,2,2-trifluoroethane.

A mixture of 10 grams (0.057 mole) of trifluoroacetophenone, 100 ml of toluene, and 5 ml of trifluoromethylsulfonic acid were refluxed, under a Dean Stark trap, for 48 hours. At the end of this period, the mixture was cooled, transferred to a separatory funnel, and extracted with water (100 ml), saturated sodium bicarbonate (100 ml), water (100 ml), then dried with magnesium sulfate. Excess toluene was removed on a rotary evaporator and the dark brown oil dissolved in petroleum ether/benzene, 500 ml (50/50, v/v). The resulting solution was passed through a silica gel column (50 g), leaving a dark band at the top of the column, and the column then washed with 500 ml of additional solvent. The fractions were combined, solvent removed, and the product crystallized from aqueous ethanol. The crystals were washed with ethanol to give 9.0 g (43%) white crystals, mp 168°–169° C.; IR (KBr) 1590 and 1495 (Ar), 1145 (C-F), 810 (parasubstituted phenyl), 740 and 690 cm$^{-1}$ (monosubstituted phenyl); NMR $\delta$ 2.15 (s, 6H), 6.90 (s, 13H); mass spectrum m/e, 340 (parent ion), 271 (P-69 base peak), 194 (P-146), 193 (P-147), 180 (P-160), 179 (P-161). Analytical: calculated for $C_{22}H_{19}F_3$; C, 77.64; H, 5.58; F, 16.76%; found; C, 78.07; H, 5.55; F, 16.4%.

EXAMPLE 2

The procedure of Example 1 was repeated with the exception that the reactants were stirred at room temperature for 48 hours instead of refluxed. At the end, there was isolated 18 g of white crystals, m.p. 168°–169° C. This material, obtained here in 93% yield, was identical in all respects to that of Example 1.

EXAMPLE 3

1,1,1-Tris-(p-tolyl)-2,2,2-trifluoroethane.

A solution of 10 g (0.056 mole) 4-methyl-trifluoroacetophenone in 100 ml toluene and 5 ml of trifluoromethylsulfonic acid were refluxed for 48 hours and worked up in the same manner as in Example 1 to yield 11.2 g (56%) of white crystals, m.p. 217°–218° C.; IR (KBr) 1605 and 1500 (Ar), 1150 (C-F), 805 cm$^{-1}$ (para-substituted Ar); NMR $\delta$ 2.15 (s, 3H), 6.9 (s, 4H); mass spectrum m/e, 354 (parent ion), 285 (P-69 base peak), 194 (P-160), 193 (P-161), 178 (P-176). Analytical: calculated for $C_{23}H_2F_8$; C, 77.96; H, 5.93; F, 16.10%; found; C, 78.15; H, 5.99; F, 15.8%.

EXAMPLE 4

1,1,1-Tris-(4-carboxyphenyl)-2,2,2-trifluoroethane.

Two grams (0.0056 mole) of the tritolyl trifluoroethane of Example 3 were added over a 30-minute period to a cooled solution of 8.4 g (0.084 moles) chromium trioxide in 67 ml acetic acid, 22 ml acetic anhydride, and 5.5 ml sulfuric acid. The temperature of the solution was maintained at 10°–15° C. for 2 hours. The resulting brown-green solution was poured into 600 ml of ice water and stirred overnight. The product was collected on a Büchner funnel and dried under vacuum overnight to yield a pale green solid. The solid material was transferred to a Soxhlet thimble and extracted with a benzene, 1,2-dimethoxyethane solution (80/20, v/v) for 24 hours. The solution was cooled and triturated with light petroleum ether. The white powder was collected and air-dried to yield 1.80 g, mp 366°–367° C.; IR (KBr) 3440 (very broad), 1690, 1570, and 1415 (COOH), 1605 and 1510 (Ar), 1150 (C-F), 810 cm$^{-1}$ (para-substituted phenyl). Analytical: calculated for $C_{23}H_{15}O_6F_3$; C, 62.16; H, 3.37; F, 12.83%; found; C, 61.99; H, 3.40; F, 13.0%.

EXAMPLE 5

1,1,1-Tris-(4-formylphenyl)-2,2,2-trifluoroethane

A mixture of 1.00 g (0.0028 mole) of 1,1,1-tris-(p-tolyl)-2,2,2-trifluoroethane, 3.1 g N-bromosuccinimide (NBS; 0.017 mole, 6.22 equivalents), and 100 mg (approximate) of benzoyl peroxide in 25 ml of carbon tetrachloride was refluxed for 6 hours, or until all of the heavier NBS (NBS d, 2.098; CCl$_4$ d, 1.5940) was entirely consumed and the lighter (d, 1.4180) succinimide floated on the surface of the solution. The product was filtered and the carbon tetrachloride evaporated under anhydrous conditions to give the desired hexabromide which was used without purification in the next step.

A solution made from dissolving 0.58 g (0.02 mole) of sodium in 50 ml anhydrous methanol was added to the hexabromide and the mixture refluxed for 2 hours. At the end of the refluxing period, the solution was filtered and solvent removed in vacuo to yield an oil which solidified overnight. The residue was dissolved in 25 ml dioxane, and 75 ml water and 5 ml conc. hydrogen chloride were added to the stirring solution. The resulting cloudy mixture was stirred at room temperature overnight. After the hydrolysis was complete, the aqueous solution was extracted 3 times with 50-ml portions of ether, dried with anhydrous magnesium sulfate, and evaporated to yield a pale yellow solid. The NMR spectrum of the crude mixture has singlets at $\delta$ 4.45 and 3.42, indicating the presence of a Ar—CH$_2$—O—CH$_3$ group. Integration of the mixture indicated that the product was approximately 90% pure trialdehyde. Column chromatography of the mixture gave 0.59 g of material approximately 90% pure, the major contaminant being a methyl ether resulting from incomplete bromination. The following data were determined: IR (CHCl$_3$) 2840 and 2740 (CHO), 1710 (C=O), 1610 and 1510 (Ar), 1140 (C—F), 810 cm$^{-1}$ (para-substituted Ar); NMR $\delta$ 7.3 (d, J-8 cps), 7.84 (d, J-8 cps), 10.04 (s).

EXAMPLE 6

1,1-Bis-(4-methoxyphenyl)-1-phenyl-2,2,2-trifluoroethane.

A mixture of 10.0 g. (0.057 mol) of trifluoroacetophenone, 10 g (0.07 mol) trifluoromethyl sulfonic acid, and 10 g (1.09 mol) anisole was stirred at room temperature for 24 hours. There was a slight initial exothermic reaction which subsided within 10 minutes. At the end of 24 hours, the mixture was transferred to a separatory funnel and the organic material was washed with water (3×100 ml), saturated sodium bicarbonate (3×50 ml), and water (2×50 ml). The organic phase was dried (magnesium sulfate) and the excess volatile reagents were removed in vacuo. The resulting non-volatile material was crystallized from aqueous methanol to give 19.9 g (94% yield) of the desired product: m.p. 120°–121° C.; IR (KBr) 1604 and 1510 (Ar); 1145 (C-F), 810 (parasubstituted phenyl), 740 and 690 cm$^{-1}$ (monosubstituted phenyl); NMR δ3.93 (s, 6H), 6.8s (d, J=4 Hz, 4H), 7.10 (d, J=4 Hz, 4H), 7.28 (s, broad, 5H); mass spectrum m/e, 372 (parent ion), 303 (P-69 base peak), 288 (P-84), 273 (P-99), 226 (P-146), 195 (P-177), 180 (P-192), 165 (P-207), 107 (P-265) 88 (P-284), 77 (P-295). Analytical: calculated for $C_{22}H_{19}O_2F_3$; C., 70.97; H, 5.12; F, 15.32%. Found: C, 71.13; H, 5.16; F, 15.1%.

EXAMPLE 7

1,1-Bis-(4-hydroxyphenyl)-1-phenyl-2,2,2-trifluoroethane.

3.72 g. (0.01 mol) of the product of Example 6 was refluxed for 18 hours in 50 ml of glacial acetic acid saturated with anhydrous hydrobromic acid. At the end of the reflux period, the product was poured over cracked ice and the gummy solid was collected. The crude material was crystallized from ethanol and petroleum ether to give 2.23 g (64.8%) of the dihydroxy derivative: m.p. 225°–226° C.; IR (KBr) 3440 (—OH); 1610 and 1510 (Ar), 1180 (phenolic-O—), 1150 (C-F), 820 (parasubstituted phenyl), 750 and 690 cm$^{-1}$ (monosubstituted phenyl). Lit. m.p. 224° C.

EXAMPLE 8

1,1-Bis-(4-hydroxy-3-nitrophenyl)-1-phenyl-2,2,2-trifluoroethane.

A solution of 2.22 g. (0.0064 mol) of the dihydroxy compound of Example 7 in 20 ml glacial acetic acid, 2 ml acetic anhydride, and 1.96 g (70% solution, 0.015 mol) of nitric acid was stirred at room temperature for 20 minutes. The resulting yellow solution was poured into ice water and the solid product was collected. The crude mass was crystallized from aqueous alcohol to give 2.07 g (74% yield) of yellow crystals: m.p. 146°–147° C.; IR (KBr) 3420 (—OH), 1640 L and 1490 (Ar), 1535 and 1335 (—NO$_2$), 1180 (phenolic), 1150 (C-F), 760 and 700 cm$^{-1}$ (mono substituted phenyl); NMR δ 7.1 (d, J=10 Hz, 2H), 7.3 (broad multiplet, 7H) 7.75 (d, J=4 Hz, 2H); mass spectrum m/e, 434 (Parent ion), 365 (P-69). Analytical: calculated for $C_{20}H_{13}O_6N_2F_3$; C, 55.29; H, 2.99; N, 6.45; F, 13.13%. Found: C, 55.29; H, 3.06; N, 6.25; F. 13.3%.

EXAMPLE 9

1,1-Bis-(4-phenoxyphenyl)-1-phenyl-2,2,2-trifluoroethane.

A solution of 10.0 g (0.059 mol) trifluoroacetophenone in 5 ml of trifluoromethyl sulfonic acid, and 50 ml of diphenyl ether was stirred for 48 hours at room temperature. At the end of this period, the product was isolated as in Example 6 to give 19.4 g (74%) of white crystals: m.p. 109°–110° C.; IR (KBr) 1590 and 1490 (Ar), 1150 (C—F), 830 (parasubstituted phenyl) 750 and 690 cm$^{-1}$ (monosubstituted phenyl); NMR δ 6.80 (d, J=8 Hz); 6.90 (d, J=8 Hz), 7.1 (s, broad); mass spectrum m/e, 496 (parent ion), 427 (P-69), 350 (P-146), 333 (P-163), 258 (P-238). Analytical: calculated for $C_{32}H_{23}O_2F_3$; C, 77.42; H, 4.63; F, 11.5%. Found: C, 77.11; H, 4.58; F, 11.6%.

EXAMPLE 10

1,1-Bis-(4-t-butylphenyl)-1-phenyl-2,2,2-trifluoroethane.

A mixture of 10.0 g (0.057 mol) trifluoroacetophenone, 100 ml t-butyl-benzene and 5 ml trifluoromethyl sulfonic acid was stirred for 48 hours. The resulting mixture was worked up as in Example 6 to yield 22.7 g (94%) of white crystals: m.p. 165°–166° C.; IR (KBr) 2960 (aliphatic C—H) 1600 and 1510 (Ar), 1150 (C—F), 820 (parasubstituted phenyl) 760 and 705 cm$^{-1}$ (monosubstituted phenyl); NMR δ 1.50 (S.9H), 6.9 (d, J=8 Hz, 2H), 7.2 (d, J=8 Hz) 7.15 (S, 7.15 δ+7.2δ, 3.5H); mass spectrum m/e, 424 (parent ion), 409 (P-15); 355 (P-69); 340 (P-84) 325 (P-99), 283 (P-141). Analytical: calculated for $C_{28}H_{31}F_3$; C, 79.25; H, 7.31; F, 13.4%. Found: C, 79.54; H, 7.33; F, 12.9%.

EXAMPLE 11

1,1-Bis-(4-ethylphenyl)-1-phenyl-2,2,2-trifluoroethane.

A mixture of 10.0 g (0.057 mol) of trifluoroacetophenone, 100 ml of ethylbenzene and 5 ml of trifluoromethyl sulfonic acid was stirred at room temperature for 48 hours. At the end of this period, the product was worked up as in Example 6, but only an oily product was obtained. An NMR spectra indicated that some secondary reaction had occurred as several unanticipated peaks were present in the spectra. The oily product was distilled under vacuo. The distillate was collected and gas chromatography indicated that the volatile fraction was a complex mixture. This mixture was separated. As the distillation residue was cooled, it formed a solid mass. This material was carefully recrystallized to give 2.1 g (10% yield) of the desired white crystalline compound: m.p. 135°–136° C.; IR (KBr) 1600 and 1510 (Ar), 1150 (C-F), 810 (parasubstituted phenyl), 750 and 700 cm$^{-1}$ (monosubstituted phenyl); NMR δ 1.35 (t, J=6 Hz, 6H), 2.7 (q, J=8Hz, 4H), 7.1 (broad aromatic, 13H); mass spectrum m/e, 368 (Parent ion), 299 (P-69), 241 (P-127), 178 (P-190), 165 (P-203). Analytical: calculated for $C_{24}H_{23}F_3$; C, 78.26; H, 6.25; F, 15.48%. Found: C, 78.28; H, 6.38; F, 15.4%.

EXAMPLE 12

1,1-Bis-(4-isopropylphenyl)-1-phenyl-2,2,2-trifluoroethane.

A mixture of 10.0 g (0.057 mol) trifluoroacetophenone, 100 ml of isopropyl benzene (cumene), and 5 ml of trifluoromethyl sulfonic acid was stirred at room temperature for 48 hours. At the end of this period, the mixture was worked up as in Example 11 to give 2.7 g (12%) of white crystalline: m.p. 148°–149° C.; IR (KBr) 1600 and 1510 (Ar), 1150 (C-F), 810 (parasubstituted phenyl); NMR δ 1.3 (d, J=7H, 12H), 2.9 (hept, J=6Hz, 2H), 7.1 (broad aromatic, 13H); mass spectrum m/e, 396 (parent ion), 395 (P-1); 327 (P-69), 328 (P-70), 312 (P-84), 311 (P-85). Analytical: calculated for $C_{26}H_{27}F_3$; C, 78.78; H, 6.82; F, 14.39. Found: C, 78.77; H, 6.85; F, 14.5%.

EXAMPLE 13

1,1-Bis-(4-fluorophenyl)-1-phenyl-2,2,2-trifluoroethane.

A mixture of 10.0 g (0.057 mol) of trifluoroacetophenone, 100 ml of fluorobenzene, and 5 ml of trifluoromethyl sulfonic acid was stirred for 48 hours at room temperature. The product was worked up as in Example 6 to give 16.6 g (84%) of white crystalline fluorophenyl compound: m.p. 92°–93° C., IR (KBr) 1600 and 1510 (Ar), 1150 (C-F), 810 (parasubstituted phenyl), 730 and 700 cm$^{-1}$ (monosubstituted phenyl); NMR $\delta$ 7.15 (s, broad aromatic); mass spectrum m/e 348 (parent ion), 279 (P-69), 202 (P-146), 184 (P-164), 183 (P-165). Analytical: calculated for $C_{20}H_{13}F_5$; C, 68.96; H, 3.74; F, 27.3%. Found: C, 68.98; H, 3.81; F, 26.8%.

EXAMPLE 14

1,1,1-Triphenyl-2,2,2-trifluoroethane.

A mixture of 10.0 g (0.057 mol) trifluoroacetophenone, 100 ml of benzene, and 5 ml of trifluoromethyl sulfonic acid was stirred for 48 hours at room temperature. The product was worked up as in Example 6 to give a white crystalline mass. Thin-layer and high-pressure liquid chromatography indicated the product was a complex mixture of many components. The thin-layer chromatogram under ultraviolet light indicated the presence of many intensely white and blue fluorescent components. The product mixture was column-chromatographed on silica gel, the material then eluted with pentane, collected, and twice rechromatographed to give 6.2 g (35%), of the white crystalline triphenyl compound: m.p. 158°–159° C.; IR (KBr) 1600 and 1590 (Ar), 1150 (C-F), 760 and 695 cm$^{-1}$ (monosubstituted phenyl); NMR $\delta$ 7.18 (broad singlet); mass spectrum m/e, 312 (parent ion), 243 (P-69), 165 (P-147), 120 (P-192). Analytical: calculated for $C_{20}H_{15}F_3$; C, 76.92; H, 4.81; F, 18.2%. Found: C, 76.77; H, 4.84; F, 17.9%.

EXAMPLE 15

1,1-Bis-(4-bromophenyl)-1-phenyl-2,2,2-trifluoroethane.

A mixture of 10.0 g (0.057 mol) trifluoroacetophenone, 100 ml of bromobenzene and 5 ml of trifluoromethyl sulfonic acid was stirred for 48 hours at room temperature. The product mixture was worked up as in Example 14 to give 8.0 g (30%) of white crystalline bromophenyl compound: m.p. 97°–98° C.; IR (KBr) 1600 and 1490 (Ar), 1150 (C—F), 820 (parasubstituted phenyl) 740 and 690 cm$^{-1}$ (monosubstituted phenyl); mass spectrum m/e, 468, 470, 472 (molecular ion isotopic cluster, 468=Br$^{79}$+BR$^{79}$, 470—Br$^{79}$+Br$^{81}$, 472=Br$^{81}$+Br$^{81}$, ratio 1:2:1), 399, 401, 403 (base peak (s), P-69, ratio 1:2:1), 322 (P-148), 321 (P-149), 320 (P-150), 242 (P-228), 241 (P-229), 240 (P-230), 239 (P-231), 165 (P-305), 164 (P-306), 163 (P-307); NMR $\delta$ 7.05 (d, J=4 Hz, 4H), 7.39 (s, 5H), 7.5 (d, J=4 Hz, 4H). Analytical: calculated for $C_{20}H_{13}Br_2F_2$; C, 51.06; H, 2.76; Br, 34.04; F, 12.1%. Found: C, 51.45; H, 2.85; Br, 33.8; F, 12.3%.

EXAMPLE 16

1,1,1-Tris-(4-methoxyphenyl)-2,2,2-trifluoroethane.

A solution of 9.0 g (0.044 mol) of 4-methoxy-$\alpha,\alpha,\alpha$-trifluoroacetophenone, 90 ml of anisole and 5 ml of trifluoromethyl sulfonic acid was stirred for 48 hours. At the end of this period, the product was worked up as in Example 6 to give 14.2 g (80%) of white crystalline 9; m.p. 196°–197° C., IR (KBr) 3010 (C—H, ar), 2840 (OCH$_3$), 1610 and 1510 (Ar), 1150 (C—F) 825 cm$^{-1}$ (parasubstituted phenyl); NMR $\delta$ 3.80 (s, 3H), 6.75 (d, J=8 Hz, 2H); 7.05 (d, J=8 Hz 2H); mass spectrum m/e, 402 (parent ion), 333 (P-69), 163 (P-239), 135 (P-267). Analytical: calculated for $C_{23}H_2O_3F_3$; C, 68.65; H, 5.22; F, 14.2%. Found: C, 68.48; H, 530; F, 14.2%.

The new products described as well as others which can be prepared by the process of this invention, can be employed as intermediates in organic synthesis or as comonomers or crosslinking agents in the formation of temperature-resistant polymers, depending of course on the nature of the functional group present in a particular compound.

What is claimed is:

1. 1,1,1-Triaryl-2,2,2-trifluoroethane of the formula

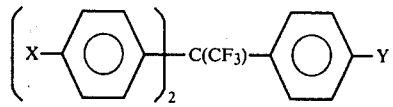

wherein X and Y are hydrogen or halogen atoms, or radicals selected from the class consisting of methoxy, phenoxy, hydroxy, alkyl of up to 5 carbon atoms, trifluoromethyl, carboxy, formyl, and nitro.

2. A process for the formation of a triaryl-2,2,2-trifluoroethane which comprises the condensation reaction of an $\alpha,\alpha,\alpha$-trifluoroacetophenone with a phenyl compound in the presence of a catalytic quantity of trifluoromethylsulfonic acid.

3. The process of claim 2 wherein the aromatic ring of the acetophenone is substituted in the para position with an halogen atom or with a radical selected from the class consisting of the methoxy, phenoxy, alkyl of up to about five carbon atoms, trifluoromethyl, amino and nitro.

4. The process of claim 2 wherein the phenyl compound is substituted with halogen atoms or radicals selected from the class consisting of the methoxy, phenoxy, alkyl of up to about five carbon atoms, trifluoromethyl, amino and nitro.

5. The process of claim 2 wherein the condensation reaction is carried out by stirring the reaction mixture at ambient temperature for a period of up to about 48 hours.

6. The process of claim 2 wherein the reaction mixture is refluxed in benzene or toluene for up to about 24 hours.

* * * * *